US00PP16574P3

(12) United States Plant Patent
Baker, Sr.

(10) Patent No.: US PP16,574 P3
(45) Date of Patent: May 23, 2006

(54) SUGAR MAPLE TREE NAMED 'BAKRISE'

(50) Latin Name: *Acer saccharum*
Varietal Denomination: BAKrise

(75) Inventor: Robert W. Baker, Sr., West Suffield, CT (US)

(73) Assignee: Baker West, Inc., Hubbard, OR (US)

( * ) Notice: Subject to any disclaimer, the term of this patent is extended or adjusted under 35 U.S.C. 154(b) by 143 days.

(21) Appl. No.: 10/879,375

(22) Filed: Jun. 28, 2004

(65) Prior Publication Data

US 2005/0289676 P1 Dec. 29, 2005

(51) Int. Cl.
*A01H 5/00* (2006.01)

(52) U.S. Cl. ..... Plt./224

(58) Field of Classification Search ..... Plt./224
See application file for complete search history.

*Primary Examiner*—Anne Marie Grunberg
(74) *Attorney, Agent, or Firm*—Klarquist Sparkman, LLP

(57) ABSTRACT

A sugar maple tree named 'BAKrise' having brilliant red fall foliage and an upright, spreading growth habit.

8 Drawing Sheets

Latin name of genus and species: *Acer saccharum.*
Variety denomination: 'BAKrise'.

BACKGROUND OF THE INVENTION

The present invention relates to a new and distinct variety of *Acer saccharum* that has been given the varietal name 'BAKrise'. *Acer saccharum* trees are indigenous to Connecticut, growing in parkways and lawns along the streets in the community of Suffield, Conn. and in the surrounding forest areas. I gathered seeds from these trees and planted and grew them in seedbeds at my nursery in West Suffield, Conn. in 1980–82. From these nursery row plantings, the applicant tree was selected in 1993.

Although the parentage of this tree is unclear, it is definitely an *Acer saccharum* tree.

I was observing the *Acer saccharum* trees lined out and growing in my nursery rows, seeking one that displayed unusual and unique fall coloring and at the same time had an attractive shape and acceptable size for home and commercial landscape settings. The new tree was discovered and selected for its bright red fall foliage and its upright, spreading growth habit.

BRIEF SUMMARY OF THE INVENTION

As I observed the original tree of my new variety, the uniqueness of this tree became apparent because of its display of brilliant red fall leaf color presentation. In particular, the leaves of my new variety matured earlier in the fall than most *Acer saccharum* varieties and held its color late into the fall season. Compared to other *Acer saccharum* varieties, the new variety of tree grows more vigorously, adding 36 inches per year or more in its earlier life. In addition, my new variety exhibits strong upright growth with ascending branches becoming broad and full at the crown, and displays dense foliage. My new variety demonstrates strong disease and insect resistance and winter hardiness. This combination of characteristics distinguish my new tree from other *Acer saccharum* of which I am aware.

My new variety was asexually propagated by beginning budding in 1997 at my direction, in Hubbard, Oreg. as follows. Bud wood was taken from the discovered tree growing in Connecticut and budded on to one to two year old *Acer saccharum* seedling under stock growing in field rows at a nursery in Hubbard, Oreg. The asexually propagated trees are true to type.

The seed that grew into this variety was planted with other seeds in a nursery seedbed at a nursery in West Suffield, Conn. The resulting trees, including the tree of my new variety, were transplanted to nursery rows four years later. In 1993, I selected the tree of my new variety. The original tree of my variety is now about 22 years old. The earliest asexually reproduced trees are about 7 years old.

The seed and pollen parent trees that produced the seeds that were planted at the nursery cannot be identified as they came from among the trees growing in the community. However, the patent applicant tree displays a much brighter fall red leaf color than any of the trees in the community.

BRIEF DESCRIPTION OF THE DRAWINGS

The accompanying photographs depict the color of the tree and foliage of my new variety as nearly true as is reasonably possible to make the same in a color illustration of this character.

DETAILED BOTANICAL DESCRIPTION

Figure 1:
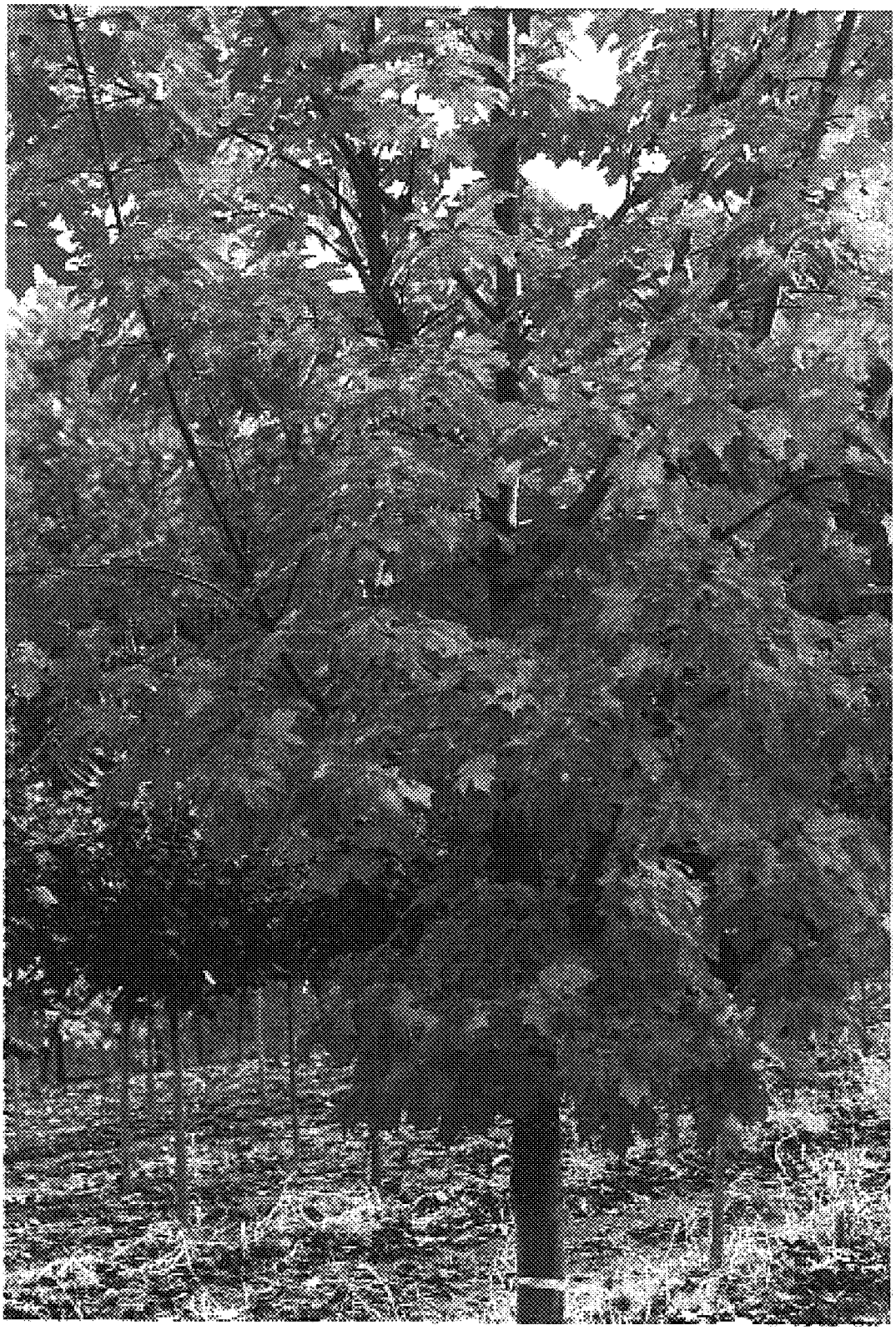
FIG. 1 is a photograph of a seven year old asexually propagated tree of my new variety showing the moderate upright growth habit and orange-red leaf color of trees at this age.
Figure 2:
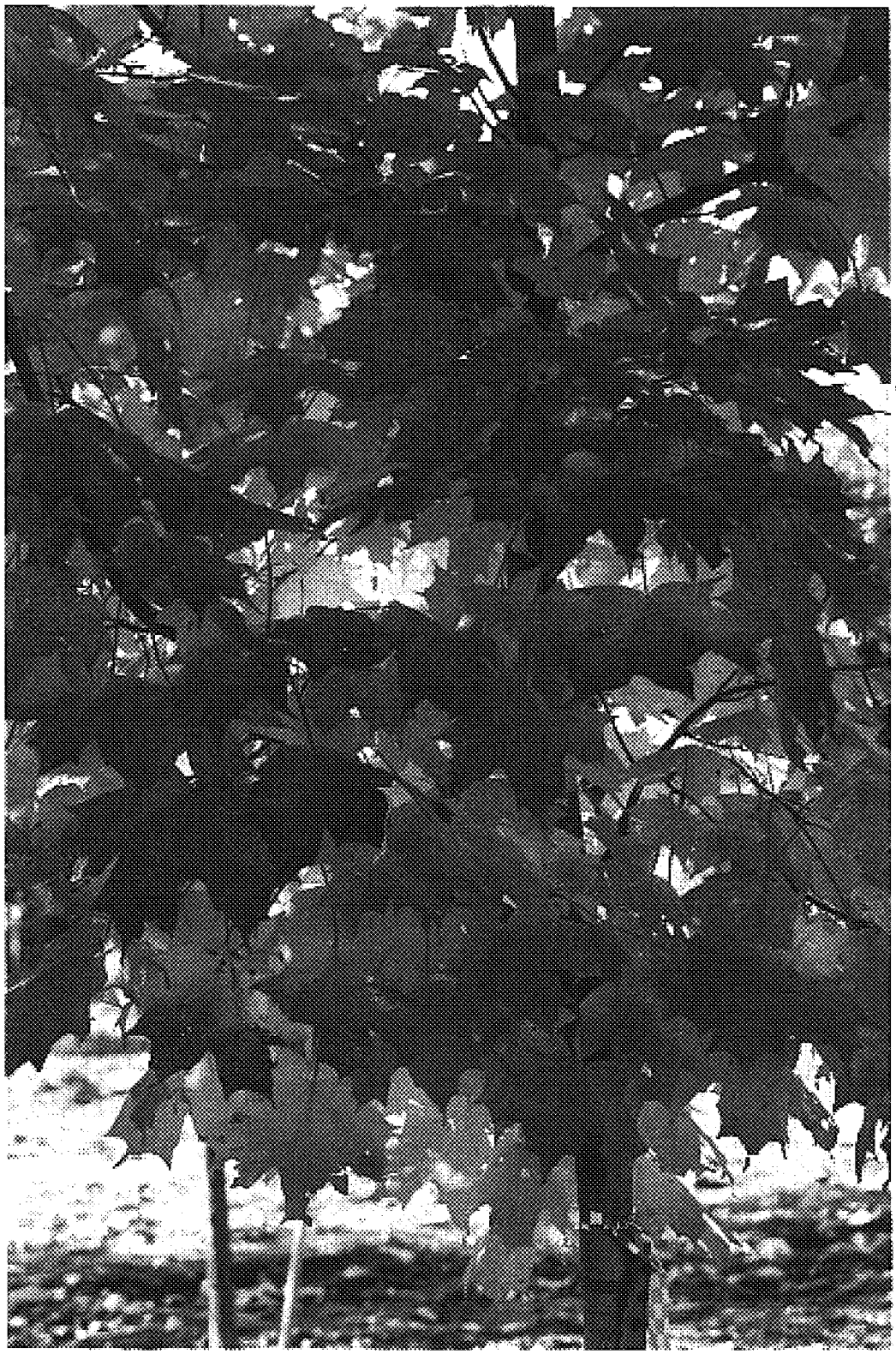
FIG. 2 is a photograph of a seven year old asexually propagated tree of my new variety showing the orange red leaf color before turning to brilliant reds.
Figure 3:
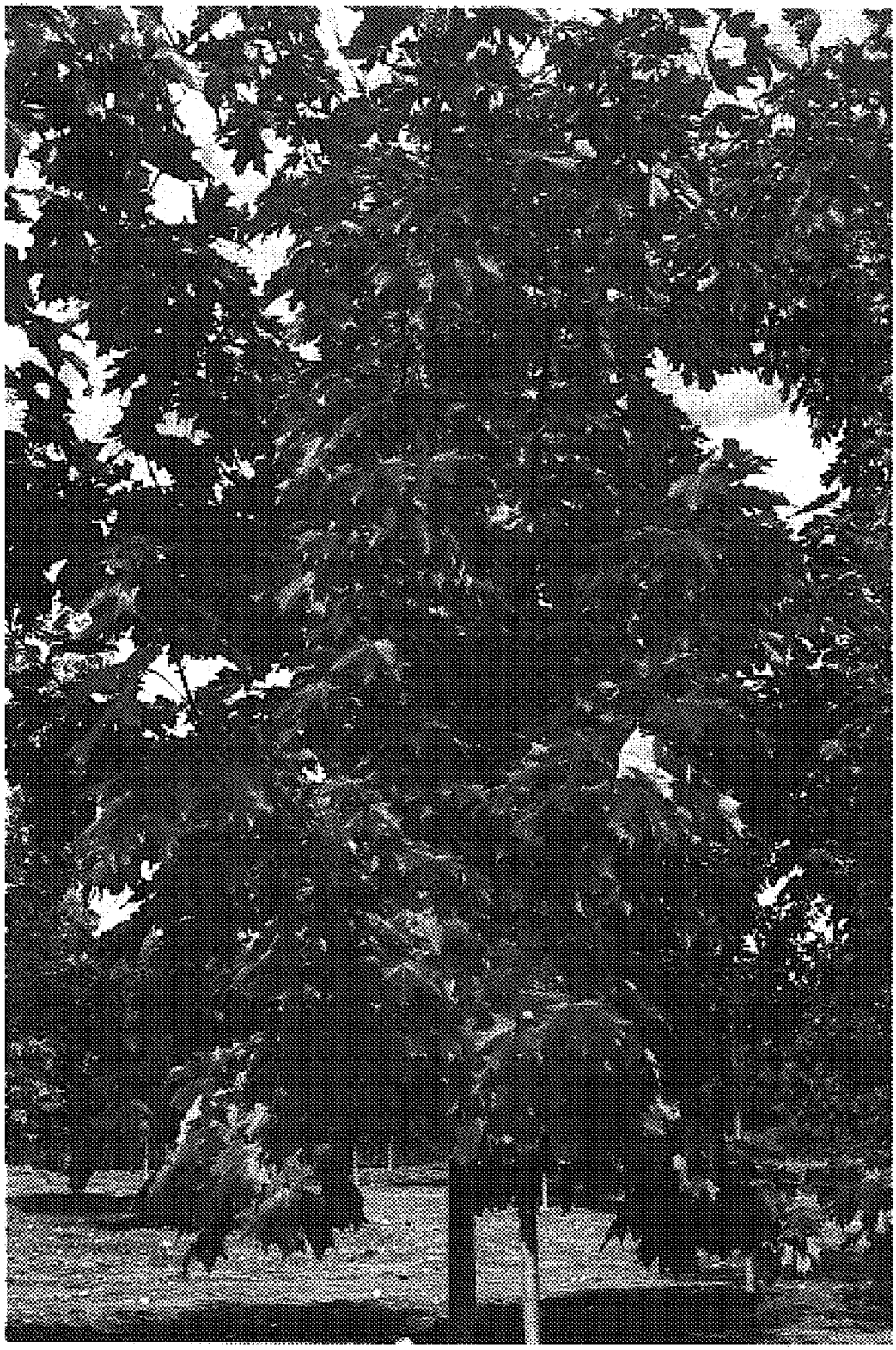
FIG. 3 is a photograph of a six-year-old asexually propagated tree of my new variety showing the moderate upright growth habit and brilliant red leaf color of trees at this age.
Figure 4:
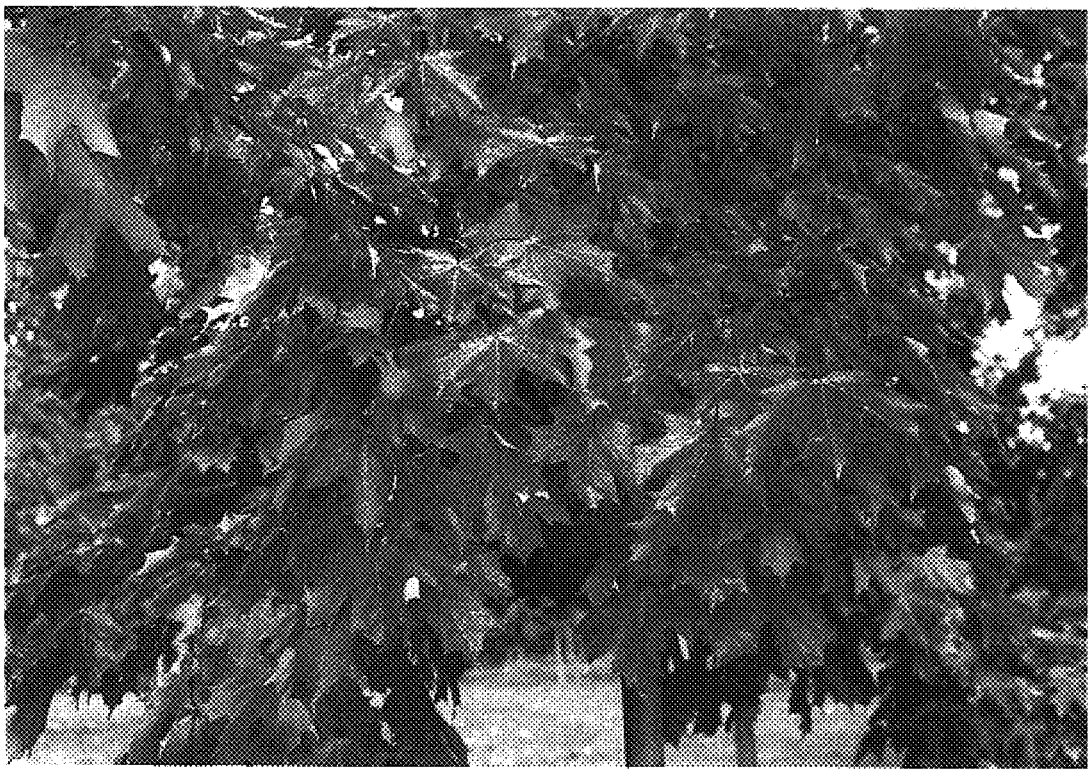
FIG. 4 is a photograph of a tree of my new variety showing leaf growing habit and brilliant red lead color.
Figure 5:
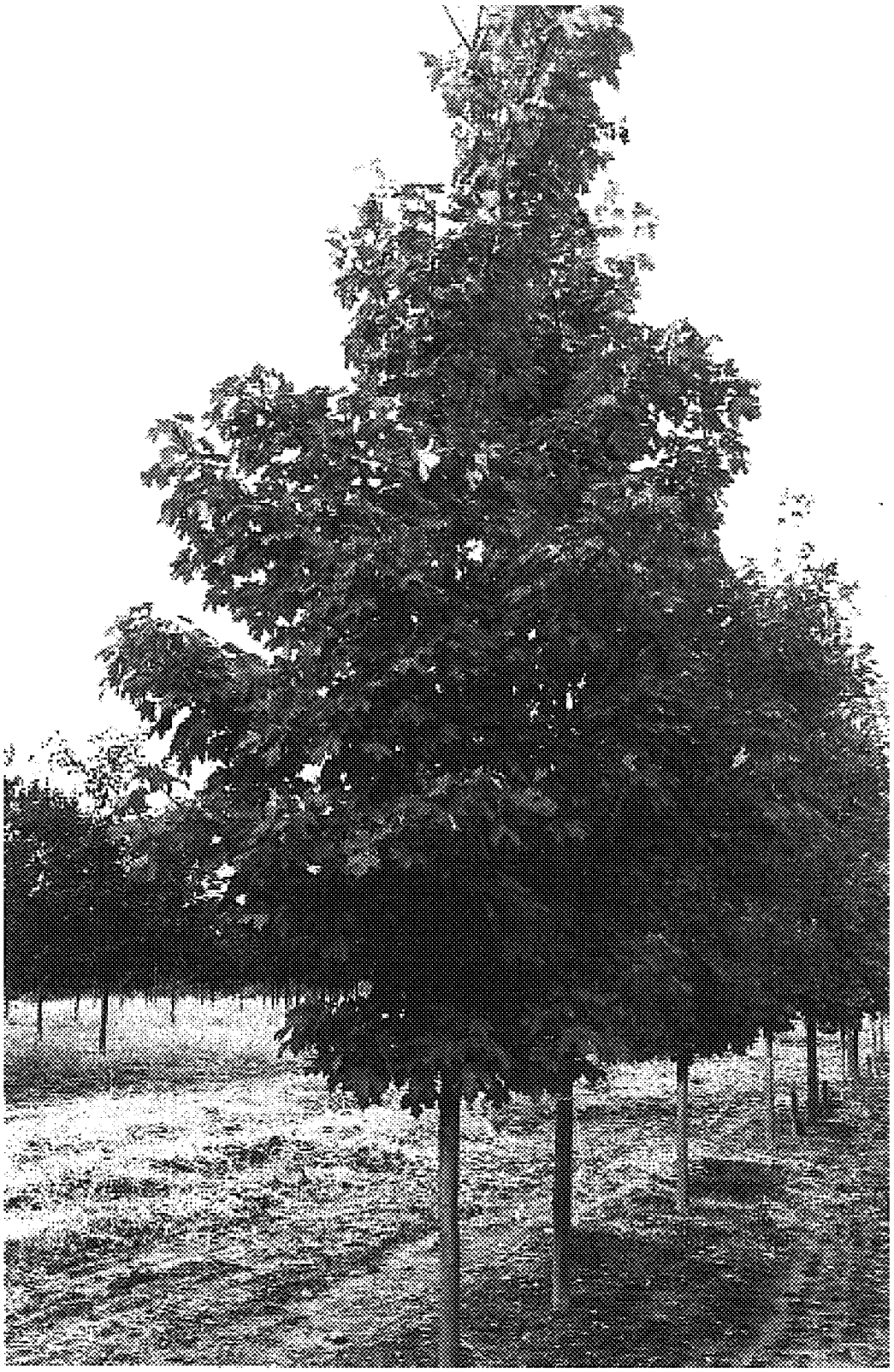
FIG. 5 is a photograph of a seven year old asexually propagated tree of my new variety showing the moderate upright growth habit of trees at this age.
Figure 6:
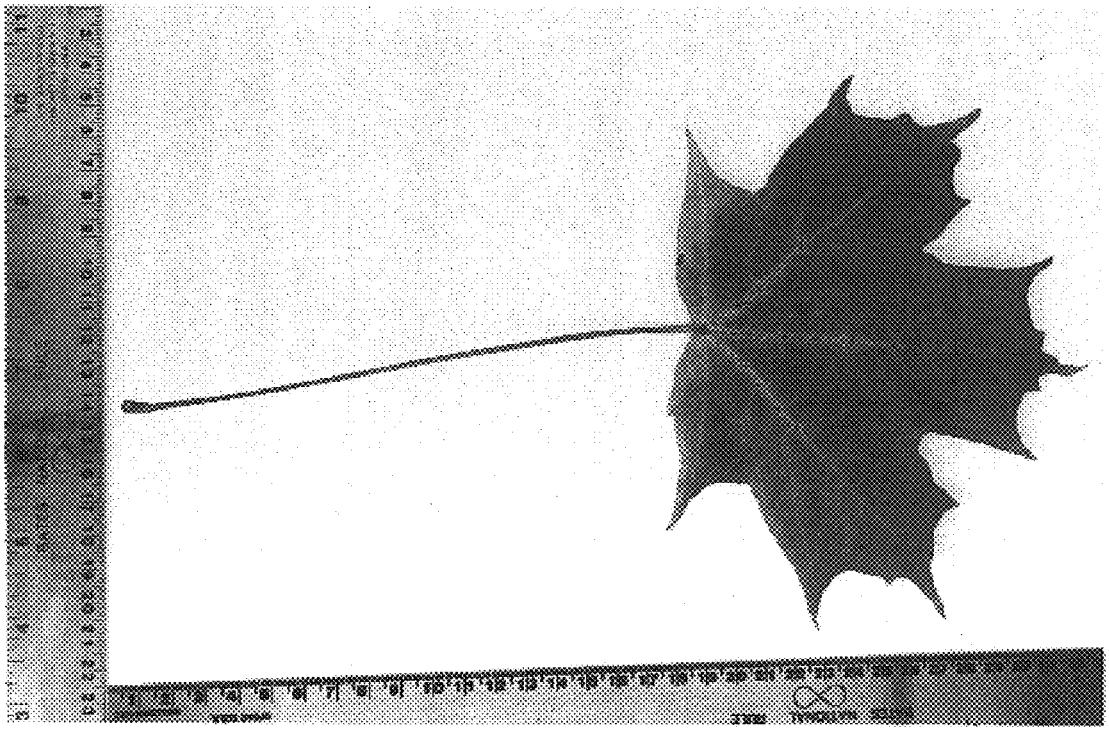
FIG. 6 is a photograph of a leaf typical leaf structure and size of my new variety.
Figure 7:
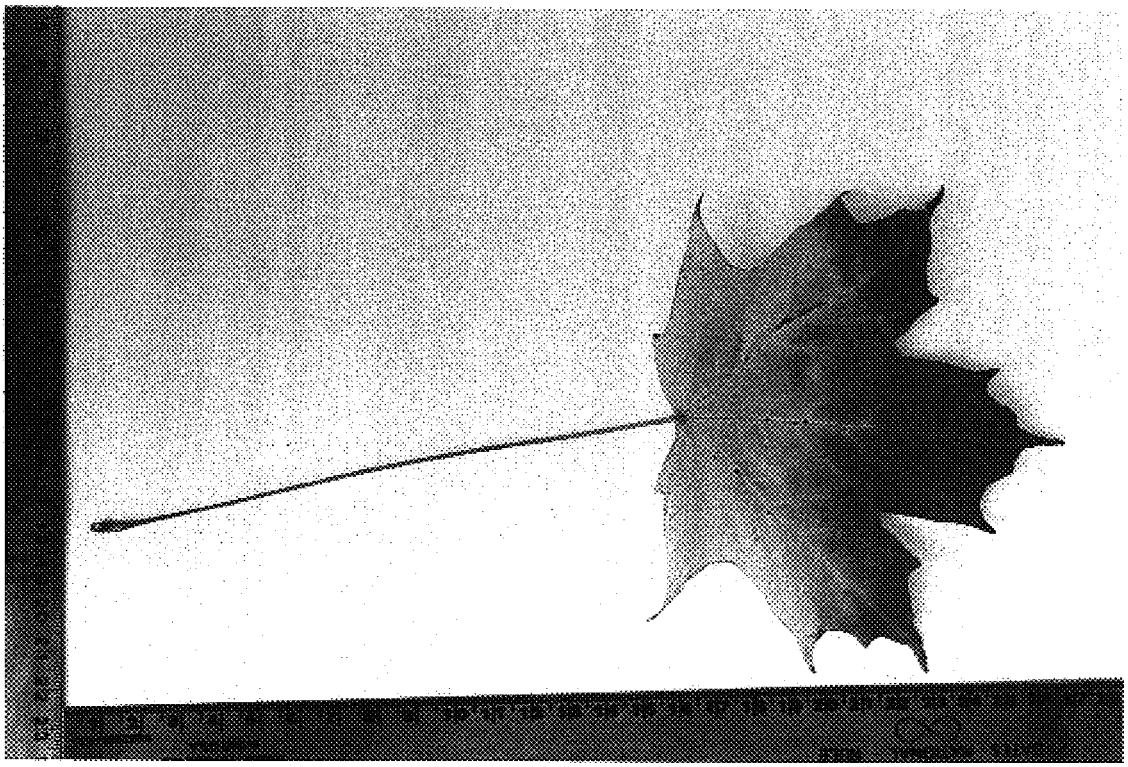
FIG. 7 is a photograph of a typical leaf typical leaf structure and size of my new variety.
Figure 8:
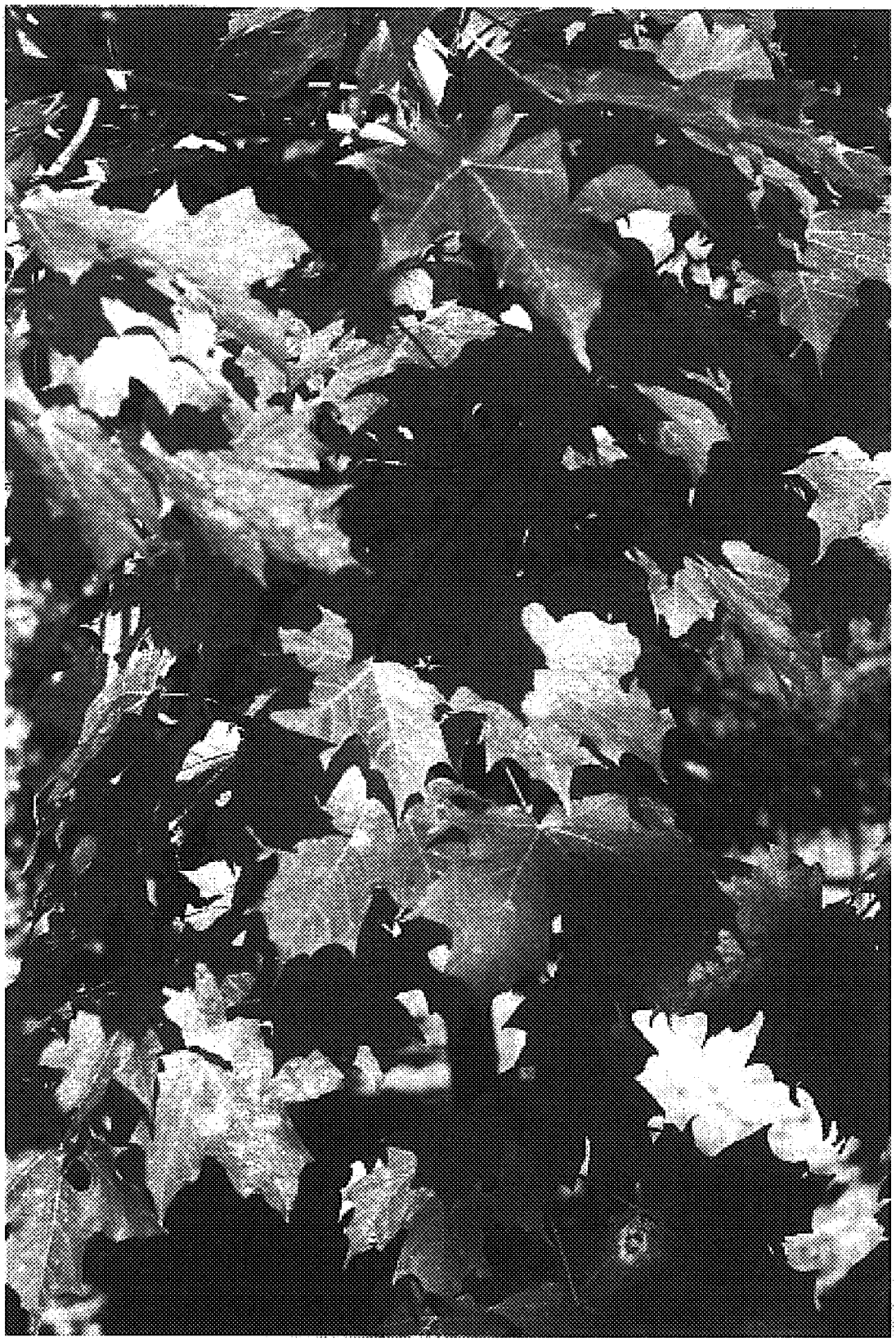
FIG. 8: is a photograph of my new variety showing typical leaf habit and early red coloring.

My BAKrise variety of *Acer saccharum* is currently growing in a nursery field near West Suffield, Conn. Asexually reproduced trees were grown in nursery fields for two years at a nursery in Hubbard, Oreg. They were dug in February 1998 and transported (February 26th) to a nursery in West Suffield, Conn. and planted directly into an open nursery field in rows.

My new tree has not been observed under all growing conditions, and thus, variations may occur as a result of different growing conditions. The following is a detailed description of my new variety of tree with color terminology in accordance with The Royal Horticultural Society (R.H.S.) Colour Chart published by The Royal Horticultural Society in London. The observations are of the original tree and of six to seven year old asexually propagated trees of my new variety growing in a nursery in West Suffield, Conn.

Trees of my new variety, both the older and younger specimens, have been through seasons of drought and high moisture (spring and summer) along with very cold hard winters. The new variety consistently displays fall leaf color as described above, both in hot drought years and cool wet years. Temperature and water rates merely affected the timing of first appearance of color and the length of time color was displayed.

Parentage: Unknown. Seeds from *Acer saccharum* trees were collected and planted in seedbeds at a nursery in West Suffield, Conn. in 1980–82. From these nursery row plantings, the original tree of my new variety was selected in 1993. My new variety of tree was discovered and selected for its brilliant red fall colors and its upright, spreading growth habit.

Tree shape: Habit is moderate upright with lower fullness. The asexually propagated 7-year old tree of my new variety is more pear shape in appearance, with mid-branches more ascending than lower branches. The original older tree of my new variety has a rounded spreading crown with full, dense foliage and a canopy 6–10 feet in diameter.

Trunk: At age seven, the asexually reproduced trees of my new variety had a diameter of about three inches measured twelve inches above the ground.

Bark: At seven years, the bark is grey-brown (RHS 187D) and smooth. The bark on the original 22 year old tree of my new variety has a deep furrowed texture.

Branching habit: Lower branches are spreading while upper quarter of branches are ascending becoming round and spreading. 40 to 60 degree angle from the trunk at emergence. The asexually reproduced seven-year-old tree of my new variety has branches which are rough and bumpy in texture. Branches are grey-brown (RHS 199C) in color.

Branch lenticels: Narrow, vertical. Length is 1 to 2 mm. Very dense. Lighter brown (RHS 199D).

Branch internodes: Average=8 cm at seven years.

Leaf number and arrangement: Opposite, simple.

Foliage:

*Leaf size* (*sampling of typical leaves*).—Leaf (including petiole): 21.5 cm–32 cm in length and 15 cm–17 cm wide. Petiole: 10.5 cm–17.5 cm, yellow-green (RHS 154C) to fall's red-orange (RHS 33A).

*Leaf shape.*—Overall Shape: Opposite — Simple leaf. Incised margins. No serration. Three lobed, cordate. Base: Truncate to cordate. Apex: Pointed, acuminate. Leaf color in summer: Upperside: Green (RHS 134A). Underside: Green (RHS 130D). Leaf color in fall: Mixture of colors. Leaves progress through different red shades then to yellow-orange and orange-red with individual leaves progressing through different color shades. Examples of typical fall color leaf changes are as follows: red (RHS 46A) to red (RHS 47A) to red (RHS 33A) to yellow-orange (RHS 17) to orange-red (RHS 34A). Vein size: Palmate, 1 mm, yellow-green (RHS 154C). Texture: Glabrous upperside and underside.

Stipules: None.

Pest and disease resistance: Appears to be tolerant to disease, insects and drought.

Winter hardiness: Grown and observed in West Suffield, Conn. and Hubbard, Oreg. (USDA Zones 4b (−20° F. to −25° F.) to 8 (10° F. to 20° F.)).

I claim:

1. A new and distinct variety of sugar maple tree substantially as herein shown and described, characterized particularly as to novelty by its brilliant red fall foliage and an upright, spreading growth habit.

* * * * *